US008790264B2

(12) United States Patent
Sandler et al.

(10) Patent No.: US 8,790,264 B2
(45) Date of Patent: Jul. 29, 2014

(54) VIBRO-ACOUSTIC DETECTION OF CARDIAC CONDITIONS

(75) Inventors: Richard H. Sandler, Evanston, IL (US); Hansen A. Mansy, Naperville, IL (US)

(73) Assignee: Biomedical Acoustics Research Company, Evanston, IL (US)

( * ) Notice: Subject to any disclaimer, the term of this patent is extended or adjusted under 35 U.S.C. 154(b) by 356 days.

(21) Appl. No.: 13/117,589

(22) Filed: May 27, 2011

(65) Prior Publication Data

US 2011/0295127 A1 Dec. 1, 2011

Related U.S. Application Data

(60) Provisional application No. 61/349,067, filed on May 27, 2010.

(51) Int. Cl.
*A61B 5/02* (2006.01)

(52) U.S. Cl.
USPC .......................................... 600/483; 600/481

(58) Field of Classification Search
USPC ................................................ 600/481, 483
See application file for complete search history.

(56) References Cited

U.S. PATENT DOCUMENTS

| 2,294,015 | A | 8/1942 | Salb et al. |
| 6,726,635 | B1 | 4/2004 | LaSala |
| 7,022,077 | B2 | 4/2006 | Mourad et al. |
| 2002/0151789 | A1 | 10/2002 | Mansy et al. |
| 2004/0249293 | A1* | 12/2004 | Sandler et al. ............... 600/481 |
| 2006/0178589 | A1 | 8/2006 | Dobak, III |
| 2007/0038095 | A1 | 2/2007 | Greenleaf et al. |
| 2009/0306736 | A1 | 12/2009 | Dobak, III |
| 2010/0081893 | A1 | 4/2010 | Jarvik et al. |
| 2010/0087728 | A1 | 4/2010 | Jarvik et al. |
| 2011/0015704 | A1 | 1/2011 | Ternes et al. |

OTHER PUBLICATIONS

Morbiducci et al. Optical Vibrocardiography: A Novel Tool for the Optical Monitoring of Cardiac Activity. Annals of Biomedical Engineering, vol. 35, No. 1, Jan. 2007: pp. 45-58.*
"Clinical Policy Bulletin: Acoustic Heart Sound Recording and Computer Analysis," http://www.aetna.com/cpb/medical/data/600_699/0692.html, accessed on: May 18, 2011, (6 pages).
Starr et al., (Aug. 1, 1939). Studies on the Estimation of Cardiac Output in Man, and The Abnormalities in Cardiac Function, From the Heart's Recoil and the Blood's Impacts, The Ballistocardiogram. American Journal of Physiology, vol. 127, No. 1. (28 pages).

* cited by examiner

*Primary Examiner* — Navin Natnithithadha
*Assistant Examiner* — Etsub Berhanu
(74) *Attorney, Agent, or Firm* — Hanley, Flight & Zimmerman, LLC

(57) ABSTRACT

Apparatus and methods for vibro-acoustic detection of cardiac conditions are disclosed. An example method includes calculating a frequency difference between a first frequency of a first cardiac signal and a second frequency of a second cardiac signal; calculating an amplitude difference between the first cardiac signal and the second cardiac signal; calculating a root-mean-square value based on a difference between the first cardiac signal and the second cardiac signal; calculating a value based on the frequency difference, the amplitude difference, and the root-mean-square value; and detecting a cardiac condition based on the value.

49 Claims, 10 Drawing Sheets

VIBRO-ACOUSTIC DETECTION OF CARDIAC CONDITIONS

RELATED APPLICATION(S)

This patent claims priority from U.S. Provisional Application Ser. No. 61/349,067, entitled "VIBRO-ACOUSTIC DETECTION OF CARDIAC CONDITIONS USING LOW-FREQUENCY OSCILLATIONS" and filed on May 27, 2010. U.S. Provisional Application Ser. No. 61/349,067 is hereby incorporated by reference in its entirety.

TECHNICAL FIELD

The present disclosure pertains to cardiac monitoring and, more specifically, to vibro-acoustic detection of cardiac conditions.

BACKGROUND

Heart failure (HF) is a condition where the heart does not contract and relax properly, resulting in inefficient pumping action, usually due to dysfunction of a ventricle (the lower chambers of the heart). HF impairs the ability of the heart to supply sufficient blood flow to meet the needs of the body. As HF progresses, pumping efficiency decreases and the body attempts to compensate by increasing the heart muscle mass. Such compensation is commonly referred to as remodeling. The heart eventually requires more oxygen than it can obtain, which results in further damage to the heart muscle. As remodeling progresses, the walls of the heart stiffen and pumping efficiency decreases. Production of various neurohormones is another compensation mechanism that can cause further heart damage.

HF can cause a large variety of symptoms such as dyspnea (shortness of breath), exercise intolerance, fluid retention, ankle swelling, and coughing. The rapid accumulation of fluid within pulmonary interstitial and alveolar spaces results from elevated cardiac filling pressures (cardiogenic pulmonary edema). HF patients can experience heart rhythm abnormalities and lack of ventricle coordinated contractions.

HF is also associated with significantly reduced physical and mental health, resulting in a markedly decreased quality of life and is also characterized by high mortality, frequent hospitalization, and a complex therapeutic regimen. Management of HF is challenging given the heterogeneity of the patient population, absence of a universally accepted definition, incomplete understanding of the pathophysiology, and lack of robust evidence-based guidelines. The majority of patients appear to respond well to initial therapies including loop diuretics and vasoactive agents. However, post-discharge and rehospitalization rates and HF-related mortality within 3-6 months reach 20-30% and 10-20%, respectively (reflecting both the severity of HF and underlying myocardial injury, renal impairment and other diseases).

Heart failure is often undiagnosed due to the lack of a universally agreed definition and challenges in definitive diagnosis. Treatment commonly involves lifestyle measures (such as decreased salt intake) and medications, and sometimes devices or even surgery. With the exception of heart failure caused by reversible conditions, the condition usually worsens with time and is associated with an overall annual mortality rate of 10%.

There are an estimated 5 million patients currently suffering from HF in the US, with a burden of about 1 million US hospitalizations and direct and indirect costs over $35 billion annually. HF has increased significantly over the past decades and is likely to increase further with better treatments for myocardial infarction, an aging population, and improved strategies for sudden cardiac arrest prevention.

Given the huge economic impact of HF hospitalizations, many strategies have been used to prevent inpatient stays including direct patient visits by physicians or other healthcare providers, patient disease management systems (including daily weights, scales, symptom assessment, etc.), and implantable devices using hemodynamic measurements or trans-thoracic impedance as surrogate markers of decompensating HF. The methods and apparatus described herein can be used in a non-invasive fashion, or along with other invasive methods, to provide increased monitoring and diagnosis utility.

To determine the best course of therapy, physicians often assess the stage of heart failure according to the New York Heart Association (NYHA) functional classification system. This system relates symptoms to everyday activities and the patient's quality of life. The table below shows this well-known classification.

TABLE 1

Classes of heart failure stages and their associated patient symptoms.

| Class | Patient Symptoms |
|---|---|
| Class I (Mild) | No limitation of physical activity. Ordinary physical activity does not cause undue fatigue, palpitation, or dyspnea (shortness of breath). |
| Class II (Mild) | Slight limitation of physical activity. Comfortable at rest, but ordinary physical activity results in fatigue, palpitation, or dyspnea. |
| Class III (Moderate) | Marked limitation of physical activity. Comfortable at rest, but less than ordinary activity causes fatigue, palpitation, or dyspnea. |
| Class IV (Severe) | Unable to carry out any physical activity without discomfort. Symptoms of cardiac insufficiency at rest. If any physical activity is undertaken, discomfort is increased. |

DETAILED DESCRIPTION

The example apparatus, methods and articles of manufacture described herein may be used to detect heart conditions via vibrations or acoustic signals. More specifically, the example vibro-acoustic detection methods and apparatus described herein may be used to detect vibrations or sounds caused by heart movement and blood flow. Sensors placed near, at, or below the skin surface may be used to convert heart-induced vibrations or sounds into electrical signals that are subsequently processed to determine or detect one or more condition within the underlying cardiovascular structure(s). The electrical signals may be processed to generate temporal and/or spectral information that may be indicative of a condition such as, for example, heart dysfunction. For instance, the temporal and/or spectral information generated using the methods and apparatus described herein may be used to assess a heart failure condition of a patient by comparing the generated temporal and/or spectral information to reference temporal and/or spectral information that is associated with a predetermined normal state, a different heart failure class condition, and/or a baseline condition associated with a particular subject or patient. Thus, the acoustic detection methods and apparatus described herein may be used to non-invasively determine if a cardiac condition, a cardiac compromise, or any other cardiovascular abnormality, is present.

While the example acoustic detection methods and apparatus are specifically described herein in connection with the assessment of heart failure, the example methods and apparatus are more generally applicable to a wide variety of applications and may be used to detect heart abnormalities such as, for example, congenital and structural heart disease, and valvular heart disease. For example, the acoustic detection methods and apparatus described herein may be used to detect a compromise in heart function, thereby enabling medical professionals to take measures to prevent hospitalization, morbidity, and mortality.

Figure 1:
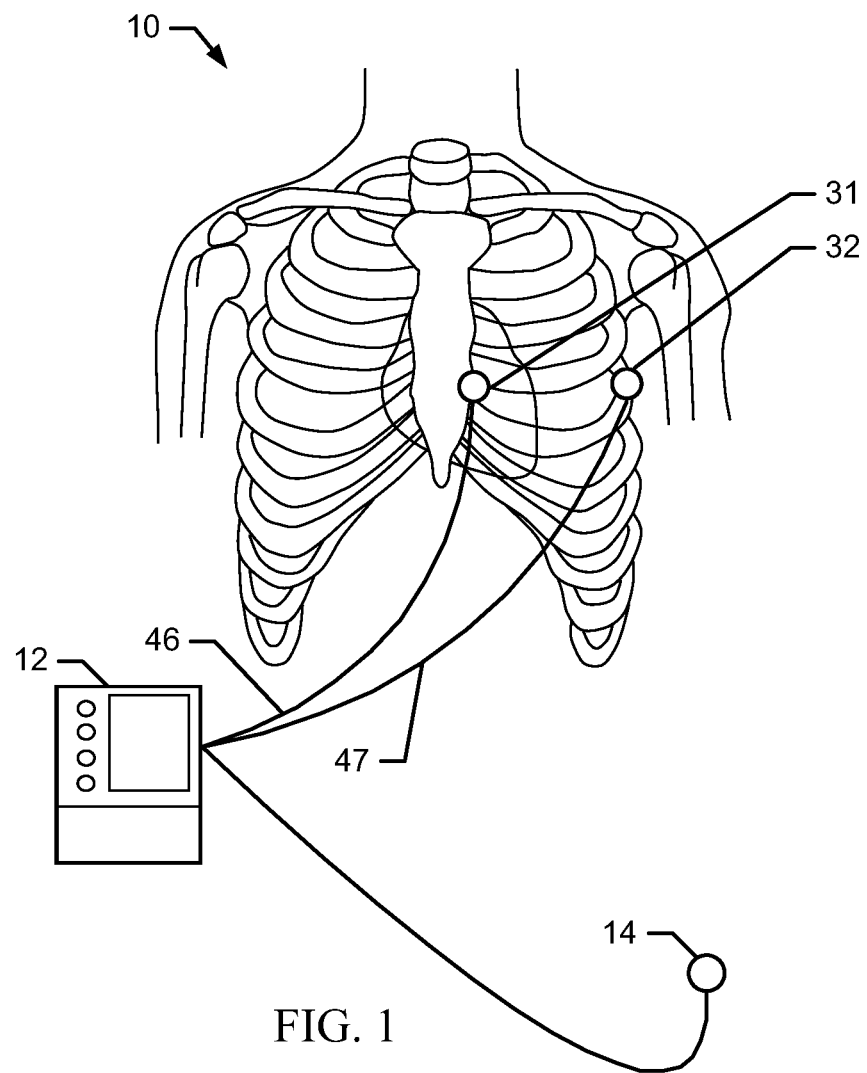
FIG. 1 is an example view of a human chest that illustrates a rib cage and heart for a typical patient and how a cardiac monitor may be attached.

The example method and apparatus described herein are also useful in screening for and identification of ischemic and inflammatory cardiac conditions, cardiac tamponade, structural heart defects, proarrythrmia pump changes to identify patients at risk for arrhythmia, distinguishing potentially hemodynamically significant from insignificant arrhythmias, dose intervention, titration and monitoring FIG. 1 is an example view of a human chest 10 that illustrates a rib cage for a typical patient and how the example apparatus may be attached to the patient The illustrated example of FIG. 1 also depicts sensors 31-32, signal communication links 46-47, a cardiac monitor 12, and an ambient noise sensor 14.

The sensors 31-32 of the illustrated example of FIG. 1 are contact transducers that detect vibrations or sounds at or near the skin surface and convert these vibrations or sounds into electrical signals. However, in some examples, the sensors 31-32 are non-contact transducers. In the illustrated example, the sensors 31-32 are accelerometers. However, any other type of sensor(s) may additionally or alternatively be used such as, for example, geophones, electronic stethoscopes, and/or contact microphones. Non-contact vibration sensors such as capacitive electromagnetic, x-ray, ultrasound, or optical sensors may additionally or alternatively be used. Further, subsurface signals can also be measured and used without departure from the scope or spirit of this disclosure. For example, subsurface tissue movement, flow movement/velocity, or flow pressure signals can be measured using M-mode ultrasound, Doppler ultrasound, or an invasive pressure transducer, respectively.

In the illustrated example, the sensors 31-32 are accelerometers that can measure low frequencies and are selected for their sensitivity over a wide bandwidth, low cost, durability, and ease of use. However, the sensors 31-32 may be any type of sensor and may be selected to suit the needs of a particular application. The sensors 31-32 of the illustrated example have an impedance that matches the impedance of the skin surface to provide optimal coupling to the skin surface. Alternatively, the impedance of the sensors 31-32 may not match the impedance of the skin. Thus, in some examples, the sensors may be attached with a double-sided tape, held by the patient, rest under the weight of the sensor, or may be attached using any past, present, and/or future method known in the art. The advantage of using a constant weight (such as sensor weight) to couple the sensor to the skin surface is an increased coupling reproducibility.

Still further, due to background noise and the relatively low amplitude of the vibrations or sounds that are generated at or near the skin surface by heart activity and/or blood flow, the sensors 31-32 may be selected to provide a high signal-to-noise ratio, high sensitivity, suitable ambient noise shrouding capability and the ability to measure low frequency signals. However, any other factors may additionally or alternatively be considered when determining which type of sensors should be used. For example, the sensors 31-32 may be selected based on their size, weight, patient comfort, and ease of use. While two sensors 31-32 are shown in the illustrated example of FIG. 1, additional or fewer sensors may be used to detect cardiac vibrations or sounds at multiple locations on the chest 10, or any other locations on the patient's body. For example, a single sensor may be strategically located on the patient's body and/or may be moved sequentially to different key locations on the patient's body to detect cardiac vibrations or sounds. While the sensors 31-32 shown in FIG. 1 are the same type of sensors (e.g., accelerometers), one or more of the sensors may be a different type of sensor. For example, the first sensor 31 may be an accelerometer while the second sensor 32 may be an M-mode ultrasonic sensor.

In the illustrated example, the sensors 31-32 can measure uni-axial vibrations (e.g., vibrations that are perpendicular to the skin or in one of the two other orthogonal directions, or in more than one direction). The cardiac monitor 12 of the illustrated example can combine the vibration measurements in all 3-directions and determine the direction of maximum and minimum vibration, which may not coincide with the three directions of measurement. This can also help identify heart-induced vibrations from patient movement during, for example, walking, which results in vibrations that tend to be non-perpendicular to the chest wall.

In the illustrated example, the ambient noise sensor 14 is added to acquire environment noise and speech. This can be used for the patient, physician, or other observer to record messages. It can also be used by the cardiac monitor 12 to remove environmental noise from measured signals using adaptive filters. Of course, any other method of noise removal may additionally or alternatively be used.

Further, sensors that detect cardiac electrical activity (e.g., electrocardiographic signals (ECG)) may additionally or alternatively be integrated for use by the cardiac monitor 12. For example, ECG measurements may be implemented by additional or alternative sensors in communication with the cardiac monitor 12. In the illustrated example, the additional sensors for measuring ECG signals are separate from the sensors 31-32. However, the additional sensors may be integrated within the same sensor.

The sensors 31-32 send signals via the signal communication links 46-47, which communicatively couple the sensors 31-32 to the cardiac monitor 12. In the illustrated example, the signal communication links 46-47 are implemented by electrical wires conducting low level (e.g., low power) electrical signals. However any other type of signal communication link(s) may additionally or alternatively be used such as, for example, a wireless radio frequency (RF) link, an infrared link, and/or a Bluetooth link. In some examples, the signal(s) carried by the signal communication links 46-47 is a signal other than an electrical signal. For example, the signal(s) of some examples are pneumatic or optical signal(s). While in the illustrated example the signal communication links are both electrical wires conducting low level electrical signals, the signal communication links need not be of the same type. For example, the first signal communication link 46 associated with the first sensor 31 may be an electrical wire while the second signal communication link 47 associated with the second sensor 32 may be a Bluetooth link.

Figure 2:
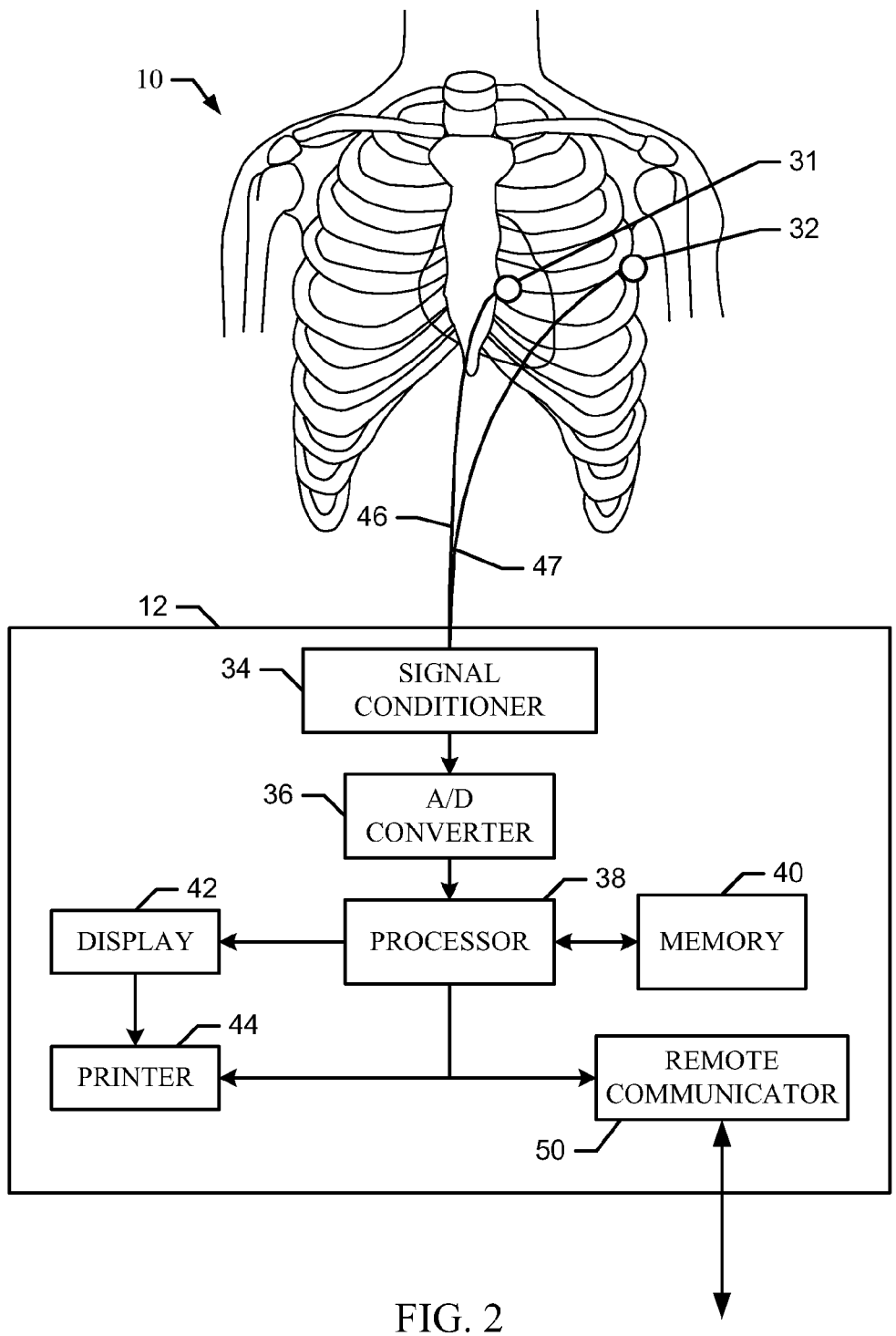
FIG. 2 is an example schematic block diagram of the cardiac monitor 12 shown in FIG. 1.

FIG. 2 is an example schematic block diagram of the cardiac monitor 12 shown in FIG. 1. As shown in FIG. 2, the example cardiac monitor 12 includes a signal conditioner 34, an analog-to-digital (A/D) converter 36, a processor 38, a memory 40, a display 42, a printer 44, and a remote communicator 50 for wired or wireless remote data transfer.

The signal conditioner 34 of some examples includes amplifiers, filters, transient protection, and other circuitry that amplifies the signals sent by the sensors 31-32, attenuates noise signals, and reduces the effects of aliasing. In particular, the signal conditioner 34 of some examples includes a low-pass filter having a cutoff frequency of about 30 Hz to remove most of the environmental, speech, breath, and gastrointestinal sounds. Alternatively or additionally, a high pass filter (e.g., having a cutoff frequency of about 1 Hz) may be incorporated within the signal conditioner 34 to attenuate undesirable noise, such as patient movement and chest wall movement due to breathing.

Alternatively or additionally, a low pass filter may be incorporated within the signal conditioner 34 to extract a low frequency signal indicative of chest wall movements due to breathing. In the illustrated example, a low pass filter having a 1 Hz cutoff frequency is used. However, any other frequency may be used as the cutoff frequency of the low pass filter. Movement of the chest wall is used to identify a respiratory breathing phase (e.g., inspiratory and/or expiratory). Additionally or alternatively, breathing phase identification may be performed using chest circumference, breathing airflow sensors, and/or any other method.

The A/D converter 36 of the illustrated example receives the conditioned analog output signals from the signal conditioner 34 and converts the received analog signal values into digital vibration information, which can be processed by the processor 38 as described in greater detail below. In the illustrated example, the processor 38 is implemented by a custom integrated circuit. However, the processor 38 may be implemented by any other processing device such as, for example, a personal computer, a microcontroller, an integrated circuit chip, a cellular phone, etc. For example, the example methods and apparatus described herein may be implemented in a Smartphone application in which the phone communicates with sensors via Bluetooth or wires.

The memory 40 is communicatively coupled to the processor 38 and may include or store machine-readable instructions that, when executed by the processor 38, cause the processor 38 to carry out the methods or processes described herein. It should be recognized that the processor 38 and the memory 40 may be integral to a personal computer or, alternatively, may be implemented using one or more custom, semi-custom, or commonly available integrated circuits. Further, the machine-readable instructions may include one or more instructions that are implemented using any of a variety of programming techniques and languages without departing from the scope and the spirit of the disclosure.

The display 42 may be any conventional video monitor or any other suitable display that communicates with the processor 38 and which can display graphic and/or textual information relating to the vascular sounds and vibrations detected by one or more of the sensors 31-32. Thus, the information generated via the display 42 may enable medical personnel to make a diagnosis of the cardiac conditions within a patient's body. For example, the display 42 may graphically represent the temporal and/or spectral characteristics of the cardiac sounds or vibrations detected at a particular location of the patient's body, which may be associated with, for example, a heart condition such as, for example, heart failure or a variety of other cardiovascular pathologies. The displayed temporal and/or spectral characteristics may then be used to determine if an abnormal cardiovascular condition exists by, for example, comparing the acquired temporal and/or spectral characteristics to reference temporal and/or spectral characteristics associated with a normal or acceptable condition and/or comparing the acquired temporal and/or spectral characteristics to a baseline condition. For example, the acquired temporal and/or spectral characteristics may be compared with temporal and/or spectral characteristics that were previously acquired for a particular patient. In addition, the acquired temporal and/or spectral characteristics may further be used to determine the type and severity of any abnormal condition(s) present. The display may also suggest a course of action based on the vibration and acoustic characteristics of the measured signals. Such suggested course(s) of action(s) may include contacting a healthcare provider and/or changing medication dosage and types and/or seeking direct care such as going to a hospital or emergency room.

The printer 44 may be used to generate hard copies of textual and/or graphical information, including the information that is displayed via the display 42. For example, numerical and graphical temporal and/or spectral information may be printed to facilitate off-line analysis of test results by medical personnel and/or to facilitate the generation of permanent test results documentation for records, reports, etc.

The remote communicator 50 of the illustrated example is used to transmit textual and/or graphical and/or vibration and acoustic information to a remote healthcare location. Additionally or alternatively, the remote communicator of some examples is used to transmit a patient location, text or voice messages, and/or information that is displayed on the display 42 from the patient to the remote healthcare provider. In some examples, the transmitted information includes patient location, alerts when certain measured values exceed certain thresholds that are chosen by the healthcare provider and/or patient. The remote communicator 50 of the illustrated example allows for two-way communication between the patient and the healthcare provider. The remote communicator 50 sends information and messages to the healthcare provider, and receives messages from the healthcare provider. The cardiac monitor 12 can then deliver that information to the patient via, for example, the display 42. Communication can include speech and text messages, transmission may be wired or wireless using electromagnetic or any other wireless system(s). In the illustrated example, cell phone technology is implemented to provide data transmission. For example, the patient can use a cell phone that connects to the cardiac monitor 12 via Bluetooth and to a cell phone network such as, for example, the Internet (and thus, a healthcare provider) simultaneously or successively to report information and get feedback, advice, and/or instructions from his healthcare provider. Feedback can be in the form of text messages and/or speech. Of course, any other method of communication may additionally or alternatively be implemented.

Before discussing the operation of the cardiac monitor 12 shown in FIG. 2 in more detail, a general discussion of the vibrational/acoustic characteristics of cardiac activities is provided below. In general, as the atria and ventricles contract, blood flow is driven in and out of these heart chambers such that it circulates in the body. The effectiveness of contractions and blood flow accelerations and decelerations cause vibro-acoustic movements that transmit to the chest surface. This signal is called a vibrocardiograhphy (VCG) signal.

Figure 7:
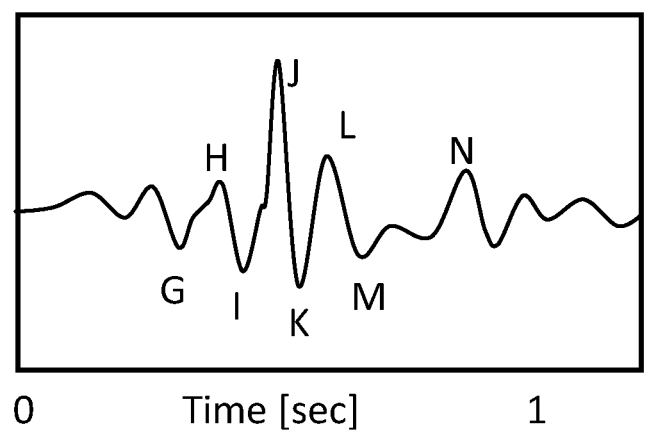
FIG. 7 is a graphical representation of an electrical signal obtained by measuring a vibrocardiograhphy waveform (VCG) at a chest wall surface.

FIG. 7 shows an example of an ideal VCG waveform that may include seven peaks and valleys, labeled H through N, as defined by the American Heart Association (AHA). The H peak is the first upward deflection of the example VCG waveform, while the L, M, and N peaks and valleys correspond to a diastolic phase of the example VCG waveform.

Respiration adds a very low frequency (<0.5 Hz) component to the VCG signal due to chest wall movement, and high frequency components (>30 Hz) due to normal and adventitial breath sounds. One example implementation removes these low and high frequencies using digital and/or analog filtering.

Figure 8A:
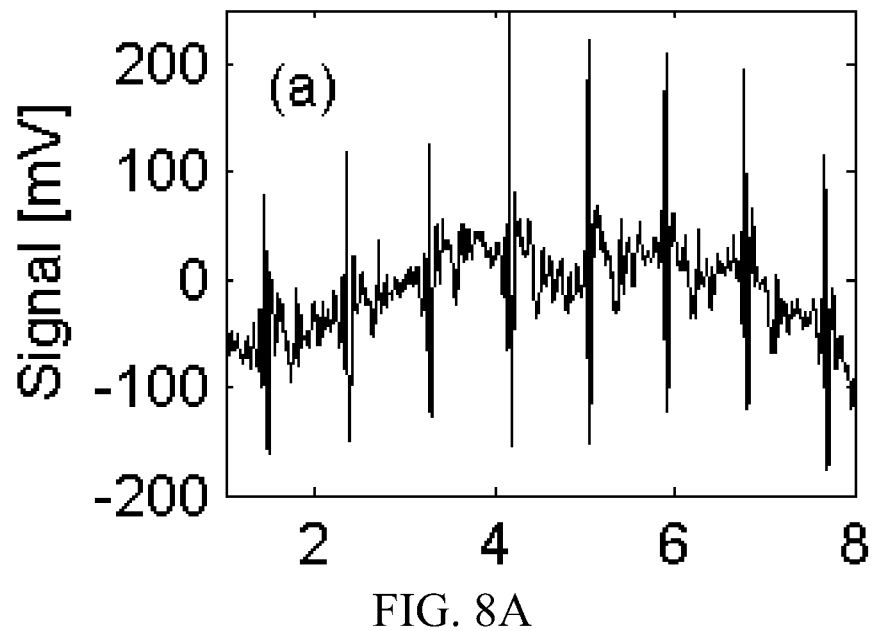
FIG. 8A is a graphical representation of a measured VCG signal containing about eight cardiac cycles.
Figure 8B:
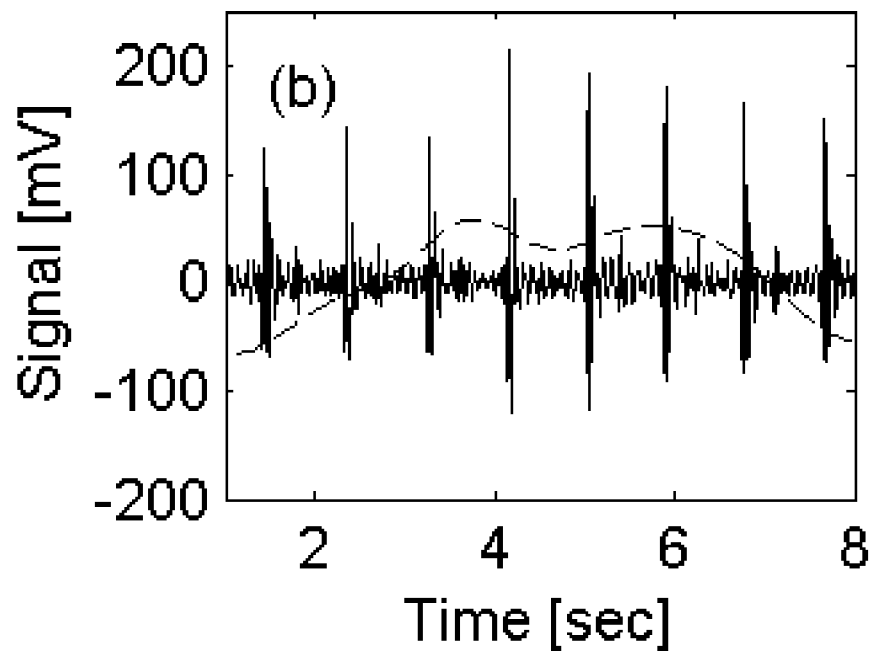
FIG. 8B is a graphical representation of a filtered form of the VCG signal of FIG. 8A showing a chest wall movement signal (dashed line) and a VCG signal (solid line).

FIG. 8A shows a measured vibrocardiographic signal before removing breath, gastrointestinal and other high frequency sounds using filtering (e.g., via a low pass filter having a 30 Hz cutoff). FIG. 8B shows the results of high pass filtering (e.g., filtering with a cutoff of 1 Hz) and low pass filtering (e.g., filtering with a cutoff of 1 Hz) to separate VCG from chest wall movements. In FIG. 8B, the chest wall movement signal is shown as a dashed line and the VCG signal is shown as a solid line.

After separating the very low frequency signal (e.g., frequencies below 1 Hz) using low pass filtering, this example uses this signal (the dashed line of FIG. 8B) to identify respiratory inspiration and expiration phases. The dashed line of FIG. 8B shows that breathing phases may be detected without the need for a separate sensor (e.g., chest expansion or airflow sensor). While this approach is shown in the illustrated example, an airflow, chest expansion, or ECG measurement can additionally or alternatively be used to find the breathing phases without departing from the scope of this disclosure. To detect breathing phases from the chest wall movement signal of (dashed line of FIG. 8B), the slope of the dashed line is calculated using a 0.1 moving average filter as described below in connection with FIG. 3 (block 124). Positive and negative slopes correspond to inspiration and expiration, respectively. The start and end times of each phase are stored in the memory 40 (block 126). In some examples, breathing sounds can be used to create separate mean VCG signals. For example, a mean VCG signal representing an average of VCG signals within a particular phase (e.g., inspiration, expiration, etc.) may be created. Further, in some examples, mean VCG signals of the inspiratory and expiratory phases may be compared to determine a value and/or variation score.

While the chest wall movement signal can be successfully removed using a high pass filter (e.g., having a cutoff of 1 Hz); (the solid line of FIG. 8B), in some examples, low frequency chest wall movements can alternatively be avoided by having the patients hold their breath. However, this can be difficult for some patients, or may even increase other noises such as respiratory system muscle sounds. Alternatively, portions of the signal containing breathing signals that can increase acquisition time may be ignored. Further, the patient may be asked to perform or may be subjected to an activity, maneuver, and/or position (e.g., holding their breath, a valsalva maneuver, a supine position, etc.) to provoke a cardiac response. For example, a VCG signal indicative of cardiac activity while the patient is involved in the activity, maneuver, and/or position may be compared against a VCG signal indicative of cardiac activity while the patient is not involved in the activity, maneuver, and/or position to determine a value and/or variation score.

The cardiac monitor 12 of the illustrated example initially analyzes time-averaged (combined inspiratory and expiratory) VCG signals. However, many cardiac abnormalities affect VCG signals during expiration before inspiration. Thus, in some examples, the cardiac monitor 12 also processes the VCG signals during inspiration and expiration separately. Metrics may be evaluated in each phase separately and may also be compared between inspiration and expiration phases. Further, metrics associated with other phases representing, for example, when the patient is performing a valsalva maneuver, when the patient is sitting, when the patient is standing, etc. may be evaluated to determine a value and/or variation score.

While an example manner of implementing the example cardiac monitor 12 has been illustrated in FIGS. 1 and 2, one or more of the elements, processes and/or devices illustrated in FIGS. 1 and 2 may be combined, divided, re-arranged, omitted, eliminated and/or implemented in any other way. Further, the example sensors 31-32, signal communication links 46-47, ambient noise sensor 14, the signal conditioner 34, the A/D converter 36, the processor 38, the memory 40, the display 42, the printer 44, the remote communicator 50, and/or more generally, the cardiac monitor 12 of FIGS. 1 and 2 may be implemented by hardware, software, firmware and/or any combination of hardware, software and/or firmware. Thus, for example, any of the sensors 31-32, the signal communication links 46-47, the ambient noise sensor 14, the signal conditioner 34, the A/D converter 36, the processor 38, the memory 40, the display 42, the printer 44, the remote communicator 50, and/or more generally, the cardiac monitor 12 could be implemented by one or more circuit(s), programmable processor(s), application specific integrated circuit(s) (ASIC(s)), programmable logic device(s) (PLD(s)) and/or field programmable logic device(s) (FPLD(s)), etc. Further, the example sensors 31-32, signal communication links 46-47, ambient noise sensor 14, signal conditioner 34, A/D converter 36, processor 38, memory 40, display 42, printer 44, remote communicator 50, and/or more generally, the cardiac monitor 12 of FIGS. 1 and 2 may include one or more elements, processes and/or devices in addition to, or instead of, those illustrated in FIGS. 1 and 2, and/or may include more than one of any or all of the illustrated elements, processes and devices.

FIGS. 3 through 6 are flowcharts representative of example processes that may be performed to implement the cardiac monitor 12 and/or components of the cardiac monitor 12. In these examples, the processes may be implemented using one or more programs for execution by: (a) a processor, such as the processor 1012 shown in the example computer 1000 discussed below in connection with FIG. 10, (b) a controller, and/or (c) any other suitable device. The one or more programs may be embodied in software stored on a non-transitory tangible medium such as, for example, a flash memory, a CD-ROM, a floppy disk, a hard drive, a DVD, or a memory associated with the processor 1012. However, the entire program or programs and/or portions thereof could alternatively be executed by a device other than the processor 1012 and/or embodied in firmware or dedicated hardware (e.g., implemented by an application specific integrated circuit (ASIC), a programmable logic device (PLD), a field programmable logic device (FPLD), discreet logic, etc.). For example, any or all of the processes represented by the flowcharts of FIGS. 3 through 6 could be implemented by any combination of software, hardware, and/or firmware. Also, one or more of the operations represented by the flowchart of FIGS. 3 through 6 may be implemented manually. Further, although the example processes are described with reference to the flowcharts illustrated in FIGS. 3 through 6, many other techniques for implementing the example methods and apparatus described herein may alternatively be used. For example, with reference to the flowcharts illustrated in FIGS. 3 through 6, the order of execution of the blocks may be changed, and/or some of the blocks described may be changed, eliminated, combined, and/or subdivided into multiple blocks.

Figure 3:
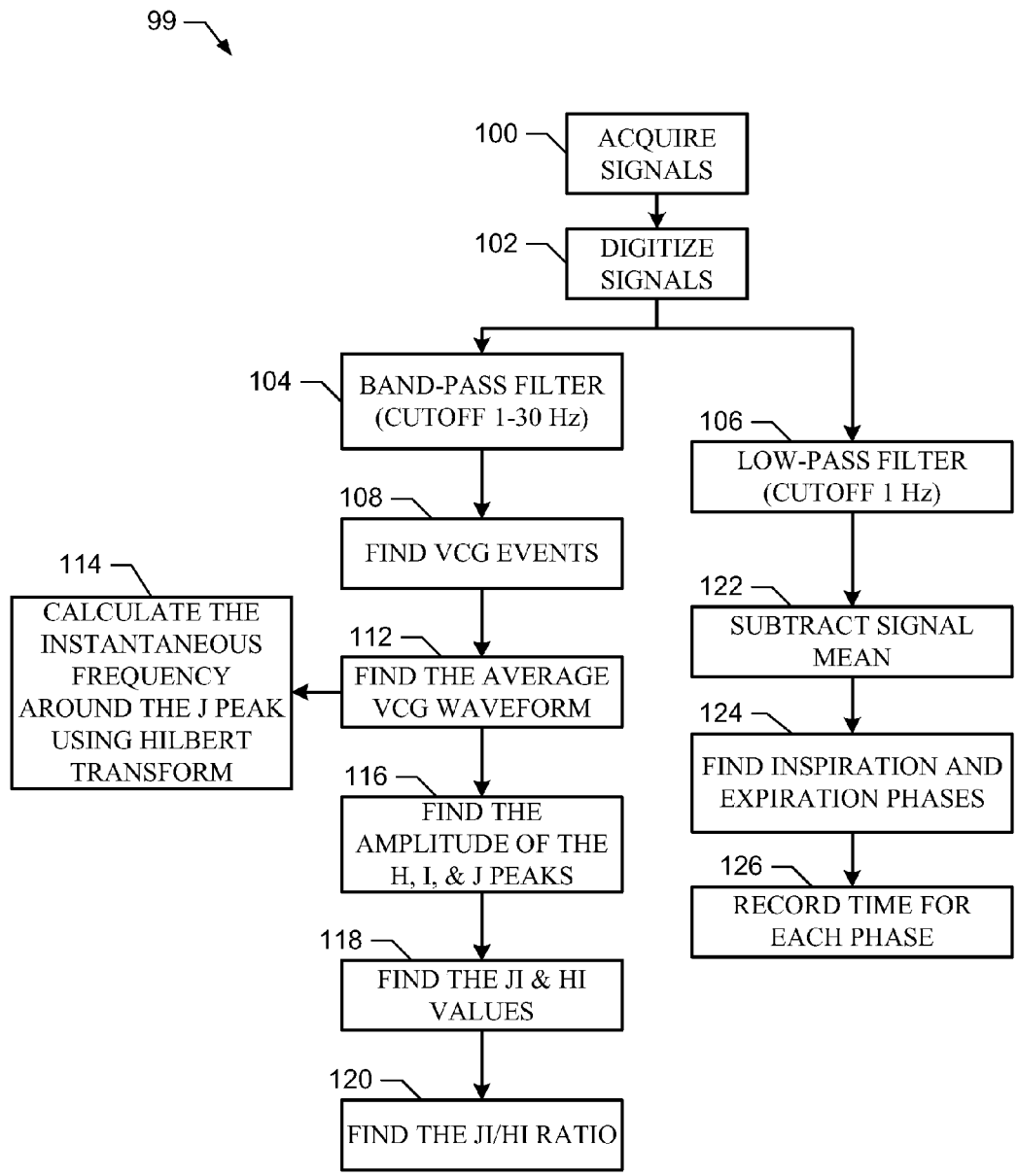
FIG. 3 is a flowchart representative of an example process that may be performed using the cardiac monitor of FIGS. 1 and 2 to process acoustic signals to assess a cardiac condition.

FIG. 3 is a flowchart representative of an example process 99 that may be performed by the cardiac monitor 12 to process acoustic signals to assess a cardiac condition. The example process 99 of FIG. 3 begins when the signal conditioner 34 acquires analog electrical signals from one or more of the sensors 31-32 (FIGS. 1 and 2) (block 100). In the illustrated example, the signal conditioner 34 may acquire signals from one or more of the sensors 31-32 for a period of time sufficient to capture cardiac sounds and vibrations that are generated during one or more cardiac cycles. For example, the signal conditioner 34 may acquire signals from one or more of the sensors 31-32 for a period of time equal to the time required to complete thirty cardiac cycles. Of course, the signal conditioner 34 may acquire sounds or vibrations for a period of time that corresponds to more or fewer cardiac cycles. In some example implementations, vibrations are acquired for about 30 seconds or longer to provide an accurate representation of the average VCG in the measured signals. However, any other time frame or period may alternatively be used. The signal conditioner 34 may filter noise, amplify the signals, etc. as discussed above before the signals are presented to the A/D converter, where the analog signals are digitized (block 102).

The sensors 31-32 may be arranged in any desired manner to facilitate the acquisition of vibrations and sounds associated with cardiac activity and to facilitate the detection of cardiac pathologies such as, for example, a heart failure condition, etc. In particular, one of the sensors 31-32 (e.g., the sensor 31) may be located directly over the fourth intercostal space at the left sternal border, which is usually an easily identifiable location, and the other sensor may be located at the heart base, apex, or some other location. Alternatively, the sensor 32 may be eliminated and only the sensor 31 may be used. Additionally, the sensor 31 may be moved to locations other than that specifically depicted in FIGS. 1 and 2 to suit the needs of a particular application. For example, the sensor 31 may be moved in sequence to measure the VCG signal at several locations.

The A/D converter 36 converts the analog signals acquired by the signal conditioner 34 into digital data or information (block 102). The analog data may be digitized at a sampling rate of 1024 Hz. However, other sampling rates may be used to achieve any desired frequency resolution. In the illustrated example, a low-pass filter with a cutoff frequency of half the sampling frequency or lower is used to avoid aliasing. However, any other type of filter may additionally or alternatively be used, and any cutoff frequency may be used to avoid aliasing. Further, the low-pass filter may be eliminated.

The signal is then filtered by the processor 38, which implements a band-pass filter to filter the digitized data provided by the A/D converter 36 (block 104). In the illustrated example, a digital filter is implemented by the processor 38. However, any other filtering techniques may additionally or alternatively be used. For example, the signal conditioner 34 may filter the signal via an analog filter before digitizing the signal in block 102. The digital filter of the illustrated example is a finite impulse response (FIR) filter. However, any other type of filter may additionally or alternatively be used such as, for example, an infinite impulse response (IIR) filter, a Butterworth filter, etc. The processor 38 additionally filters the signal using a low pass filter with a cutoff of 1 Hz (block 106). While a cutoff value of 1 Hz is used, any other value may alternatively be used.

In some examples, down sampling (i.e., re-sampling the data at a lower frequency) is performed by the processor 38 before the signal is filtered at blocks 104 and 106. Down sampling allows the filter bandwidth to be shorter, saves processing time, and improves the output of blocks 104 and 106.

Next, the processor 38 analyzes the signal to determine when each of the VCG events shown in FIG. 7 occurred (block 108). In the illustrated example, the processor 38 determines the times of the VCG events by using signal matching techniques such as, for example, the signal matching techniques discussed in connection with FIG. 5. However, any other techniques may additionally or alternatively be used. The processor 38 then determines the average VCG waveform over the period of time that samples were taken (block 112).

When an accelerometer is used to detect a VCG signal, the signal represents an acceleration that can be integrated to find a velocity, or integrated again to find a displacement signal. Integrations tend to inhibit high frequencies, thereby reducing the processing time at blocks 104 and 106. The cardiac monitor 12 can directly measure VCG signals that correspond to displacement, velocity or acceleration by using appropriate sensors without departing from the scope and spirit of the present disclosure.

The processor 38 then calculates the instantaneous frequency of the mean VCG around, for example, the J peak using a Hilbert transform (block 114). While the processor 38 implements a Hilbert transform, any other signal recognition methods may additionally or alternatively be used. The frequency is then stored in the memory 40 by the processor 38.

The processor 38 then identifies the H, I, and J peaks using the criteria that J is the global maximum, and I and H are the preceding local minimum and maximum, respectively (block 116). Next, the processor 38 calculates the HI and JI amplitudes (block 118) and then calculates the JI/HI amplitude ratio (block 120). Other ratios between different waves (including any of GHIJKLMN, or PQRS, pressure, or other waves) can be used without departing from the spirit of the present disclosure.

In parallel with blocks 108 to 120, the processor 38 receives the output of the low pass filter (block 106) and subtracts the signal mean from the signal (block 122). The processor 38 then analyzes the signal to determine start and end points of the inspiration and expiration phases (block 124). Based on the start and end points of the inspiration and expiration phases, the processor 38 determines a duration of time for both the inspiration and expiration phases and records the durations in the memory 40 (block 126).

Figure 4:
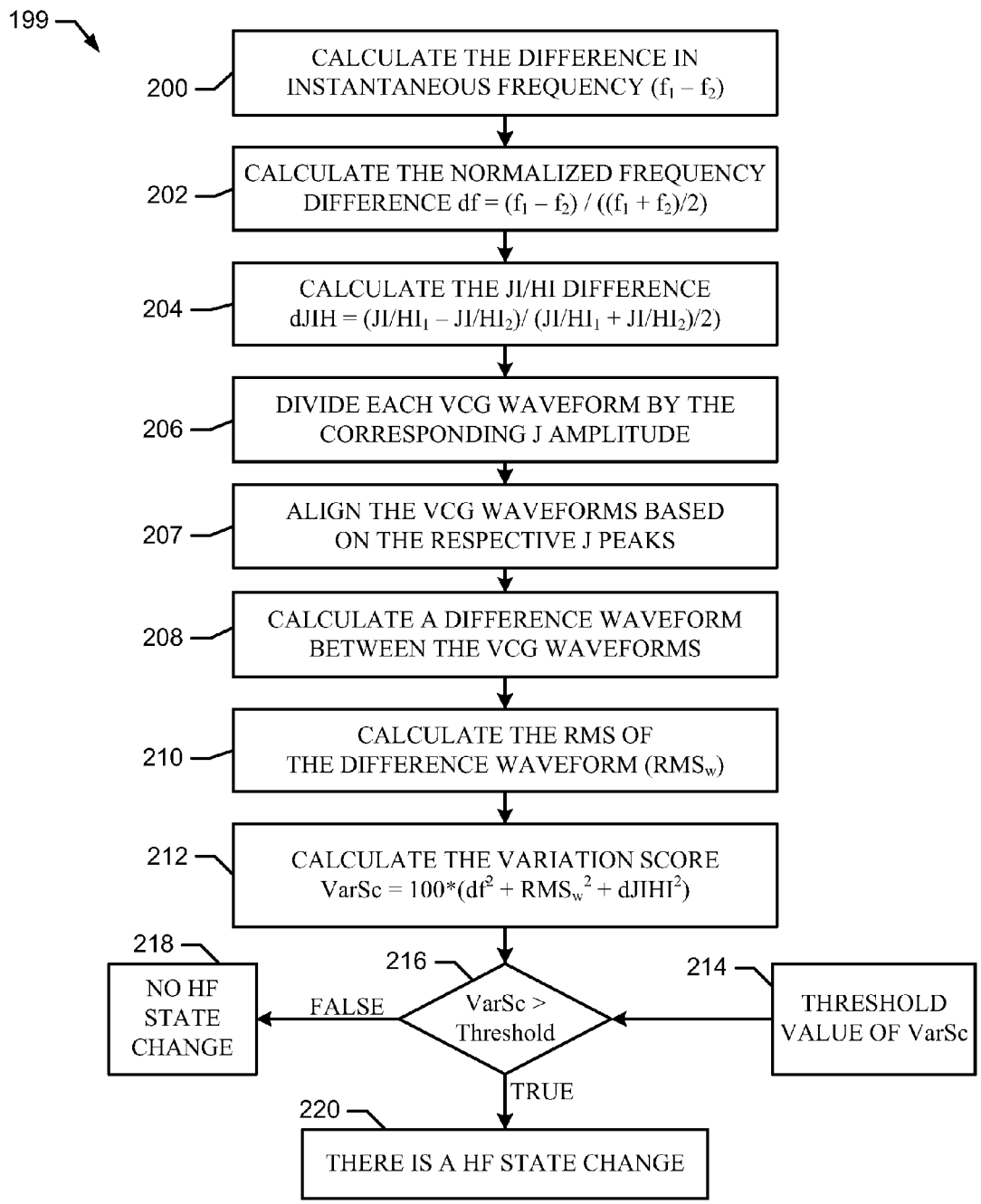
FIG. 4 is a flowchart representative of an example process that may be performed using the cardiac monitor of FIGS. 1 and 2 to implement the calculation of a value to detect a cardiac condition.

FIG. 4 is a flowchart representative of an example process 199 that may be performed using the cardiac monitor 12 of FIGS. 1 and 2 to implement the calculation of a value and/or variation score to determine a change in a cardiac condition. In the illustrated example, the variation score is calculated based on differences between two VCG waves, namely, $VCG_1$ and $VCG_2$. The example process 199 begins when the processor 38 calculates the difference between instantaneous frequencies of the two waves; $f_1$ and $f_2$ (block 200). The instantaneous frequencies $f_1$ and $f_2$ of the illustrated example are the instantaneous frequencies calculated in block 114 and are the instantaneous frequencies around the J peak of the respective VCG waves. Next, the processor 38 calculates the normalized frequency difference by subtracting the two frequencies ($f_1$ and $f_2$) and dividing by their mean (($f_1+f_2$)/2) (block 202).

The processor 38 of the illustrated example calculates an amplitude difference between the first VCG signal ($VCG_1$) and the second VCG signal ($VCG_2$) (block 204). Calculating the amplitude difference includes calculating a difference between a first amplitude ratio (e.g., the JI/HI ratio associated with the first VCG signal ($VCG_1$)) and a second amplitude ratio (e.g., the JI/HI ratio associated with the second VCG signal ($VCG_2$)). The difference between the first JI/HI ratio and the second JI/HI ratio is calculated by the processor 38. Further, in the illustrated example, the JI/HI amplitude difference is normalized by the mean of the first JI/HI ratio and the second JI/HI ratio ($dJI/HI=(JI/HI_1-JI/HI_2)/((JI/HI_1+JI/HI_2)/2)$). The amplitude difference of the illustrated example is calculated based on the J, I, and H peaks of the respective VCG waves. However, in some examples, other peaks of the VCG waves (e.g., the K peak, the L peak, the M peak) are used.

Next, the processor 38 of the illustrated example normalizes each VCG wave by dividing it by the J amplitude associated with each VCG wave (block 206). In some examples, normalization can be performed by dividing by other amplitudes. Next, the processor 38 temporally aligns the VCG waves based on the J peaks (i.e., $J_1$ and $J_2$) of the respective VCG waves (block 207). In some examples, the VCG waves are aligned using other temporal and/or spectral characteristics, such as the H peak, the I peak, etc. The processor 38 then calculates a difference waveform of the VCG waves ($VCG_1-VCG_2$) (block 208). The processor 38 then calculates the root-mean-square (RMS) of the difference waveform (block 210).

The processor 38 then combines metrics that measure the differences between the two waves, $VCG_1$ and $VCG_2$ into one metric that is called the "variation score" (VarSc) (block 212). When $VCG_1$ and $VCG_2$ are from the same or from two different VCG acquisition sessions, the score is called "intrasession variation score", or "intersession variation score", respectively. In the illustrated example, when implementing the instructions at block 212, the processor 38 combines the three metrics that are derived from the instantaneous frequency, the JI/HI ratio, and the RMS of the difference waveform. The processor 38 calculates a sum of the squares of the three metrics. In the illustrated example the sum of the squares is multiplied by one hundred. Multiplying by one hundred scales the variation score and/or value so that it is more easily interpreted by physicians, patients, etc. In some implementations, scalar values other than one hundred are used such as, for example, fifty, ten, two hundred, one thousand, etc.

Further, combining metrics using other combinations or combining more or fewer metrics can be performed without departing from the scope of spirit of the present disclosure. For example, adding the absolute values of the metrics, and/or multiplying each metric by a coefficient or by another metric is possible. One objective of combining the metrics is to provide a single (or a small number of parameters) that optimally distinguish between patients with or without a cardiac condition such as those with and without heart failure class change. The processor 38 reads from memory 40, a pre-stored threshold value (block 214) that is either preset (e.g., at the time of manufacturing), chosen by the physician, or based on history of previous measurements in the same or other patients. The processor 38 compares the variation score to the threshold value (block 216) and concludes that there is a cardiac condition (e.g., a heart failure state change) if the variation score exceeds the threshold (block 220) or that there is no cardiac condition if the variation score is below the threshold (block 218).

The comparisons of FIG. 4 are performed on the average VCG waveforms of the two different VCG recordings, which are typically collected hours or days apart. Comparing the average VCGs masks consecutive VCG-to-VCG variability. In some examples, VCG comparisons can be performed on consecutive VCGs to measure the VCG-to-VCG variability, which can be quantified by the variation score or any other metric. Here, the mean of the variation score and other statistical properties (such as standard deviation, minimum, maximum, percentiles, and inter-percentile values, e.g., differences between $75^{th}$ and $25^{th}$ percentile) are calculated. This measure of consecutive VCG-to-VCG variability and or its trend over time are additional metrics that may be used. Additionally, a comparison between mean VCG and individual VCG waveforms can be performed and the corresponding individual variation score determined. The average and other statistical properties are then calculated and are used as a measure of VCG variability within a VCG recording. These comparisons may be done in ways that are similar to the VCG-to-VCG variability above.

Figure 5:
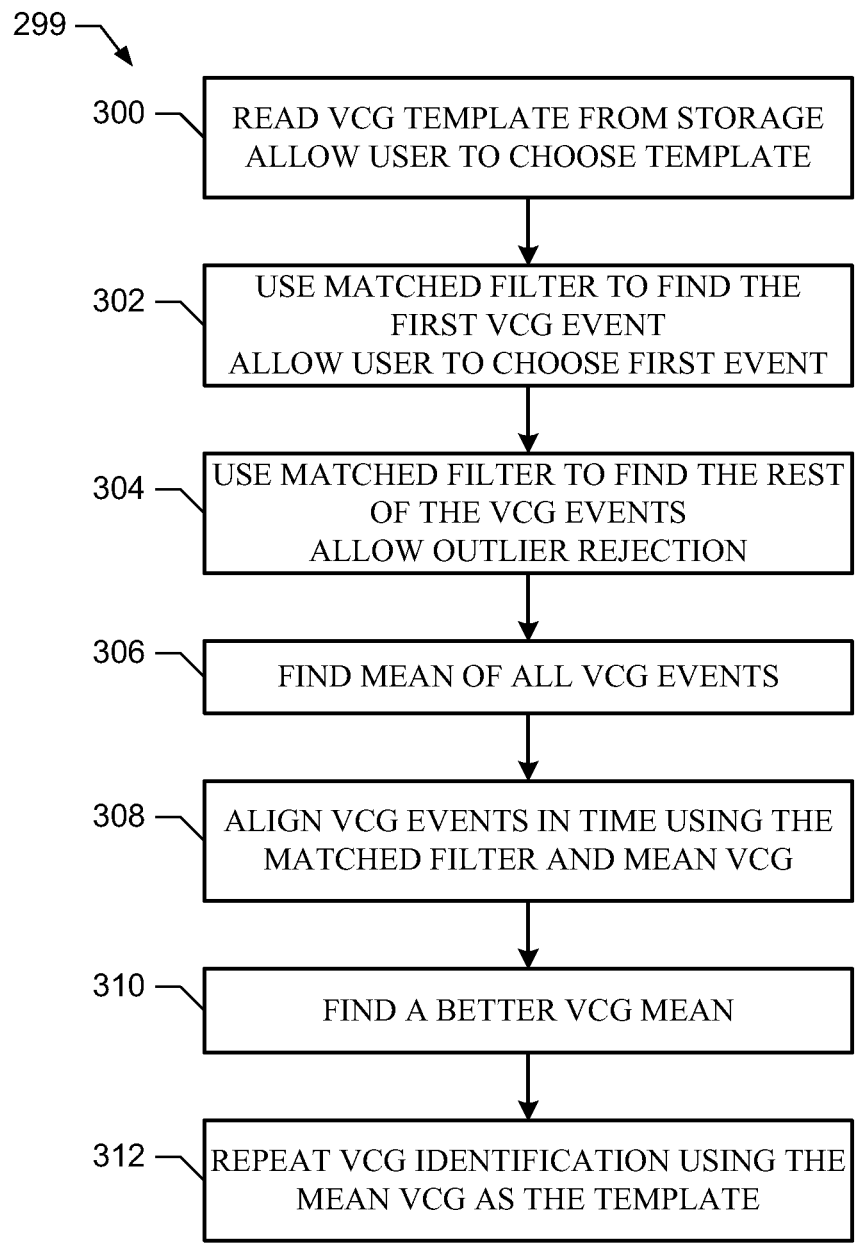
FIG. 5 is a flowchart representative of an example process that may be performed using the cardiac monitor of FIGS. 1 and 2 to detect individual vibrocardiograhphy (VCG) waveforms from VCG signals.

FIG. 5 is a flowchart representative of an example process 299 that may be performed by the cardiac monitor 12 of FIGS. 1 and 2 to detect individual VCG waveforms from VCG signals (such as that of FIG. 8A, or the solid line of FIG. 8B). FIG. 5 also shows how the mean of VCG can be calculated. The example process 299 begins when the processor 38 reads a VCG template from the memory 40 (block 300). The VCG template may be one of several pre-stored templates stored in the memory 40, and/or may be chosen or entered by the user. The processor 38 then uses the selected template to implement a matched filter to find a first VCG event (block 302). In the illustrated example, the first VCG event is identified as the J peak of the VCG waveform. However, in some examples, other events of the VCG waveform such as, for example, the H peak, and/or the I peak, may be identified as the first peak. In blocks 300 and 302, the operator is given the option to change the template choice or chose the first VCG event manually to increase identification accuracy. Once the first VCG event is identified, the processor 38 finds other VCG events in the signal using the matched filter (block 304). To save processing time, block 304 uses estimated heart rates to search for the VCG events. For example, the heart rate may be assumed to be in the range of about 30-180 beats per minute. In some examples, narrower or wider ranges of heart rates can be used. Once all events are found, the processor 38 calculates a mean VCG signal (block 306). The mean VCG signal and each individual VCG event are then input to another matched filter implemented by the processor 38 to align all VCG events in time (block 308) and find a better mean VCG event (block 310). Additionally, the mean VCG may be used as the template and the operations of blocks 302-310 are performed again (block 312). This implementation facilitates the identification of VCG events that are contained in a specific data set because the average waveform of the set represents these waveforms better than a template from the library or the first VCG chosen by the user.

Figure 6:
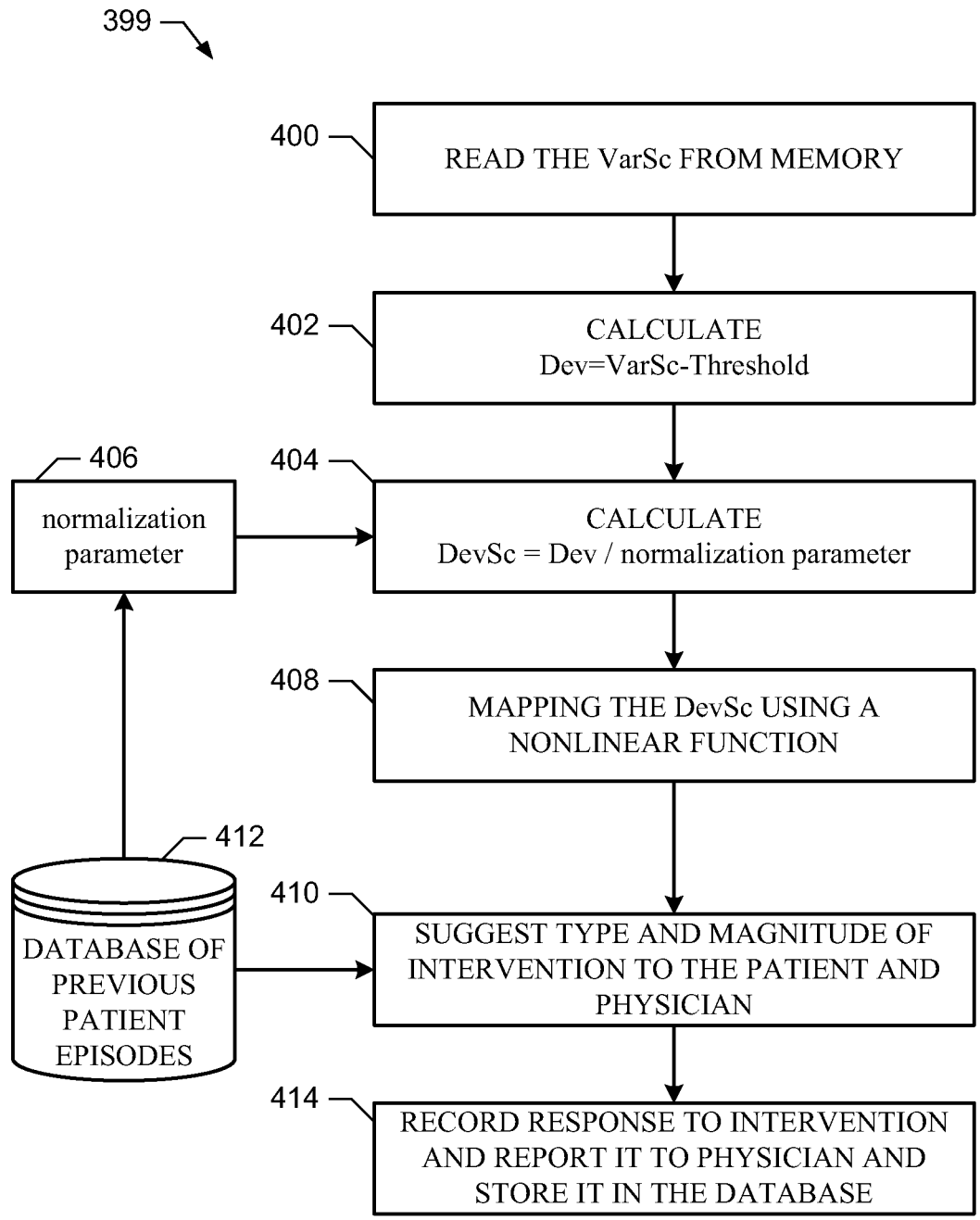
FIG. 6 is a flowchart representative of an example process that may be performed using the cardiac monitor of FIGS. 1 and 2 to determine a severity of a cardiac condition and intervention magnitude based on a difference between the variation score and a threshold.

FIG. 6 is a flowchart representative of an example process 399 that may be performed by the cardiac monitor 12 to determine a severity of a cardiac condition based on a difference between a variation score (e.g., VarSc) and a threshold. To determine the difference, the processor 38 reads the VarSc from the memory 40 (e.g., the VarSc that was calculated in block 212) (block 400). The processor 38 then calculates a difference (e.g., Dev=VarSc−Threshold) (block 402). The processor 38 of the illustrated example then retrieves a normalization parameter (block 406) from the memory 40. The normalization parameter of the illustrated example is derived from a database of previous patient episodes (block 412) and is between ten and one hundred. In some examples, the normalization parameter is below ten, and in some examples the normalization parameter is greater than one hundred. While in the illustrated example the normalization parameter (block 406) and the database of previous patient episodes (block 412) are stored in the memory 40, such information may additionally or alternatively be stored in a remote location and may be retrieved via the remote communicator 50.

After determining the normalization parameter, the processor 38 then divides the difference calculated at block 402 by the normalization parameter value (block 404). The resulting number is called a "deviation score" (DevSc), which is a measure of deviation of the cardiac condition (e.g., a heart failure state) from a baseline. The deviation score is mapped by the processor 38 using a linear or non-linear function (e.g., a polynomial of DevSc, or a function using binary or fuzzy logic) (block 408) to indicate to the patient and/or physician a suggested degree of clinical intervention (block 410). The degree of intervention of the illustrated example includes both quantitative and qualitative medication dosage and/or medication type change that the patient may need to follow to prevent or reverse the cardiac condition. In some examples, the degree of intervention includes only quantitative or qualitative analysis. Interventions also include changes in diet, patient position, physical activity, surgical procedures. Episodes of previous changes in cardiac conditions (e.g., heart failure state) and interventions are used to optimize values of the normalization parameter and mapping function to provide improved values of the recommended amount of intervention. Information concerning previous patient episodes may be retrieved from the database of previous patient episodes (block 412) which may be stored locally or remotely (e.g., in the memory 40). Any other adaptive procedure can be used to optimize the intervention amount without departing from the scope and spirit of this disclosure. The cardiac monitor 12 continues to record VCGs to follow the response to intervention and reports that information to the physician and stores it in a database (block 414). The database may be stored in the cardiac monitor 12 and/or remotely.

Figure 9:
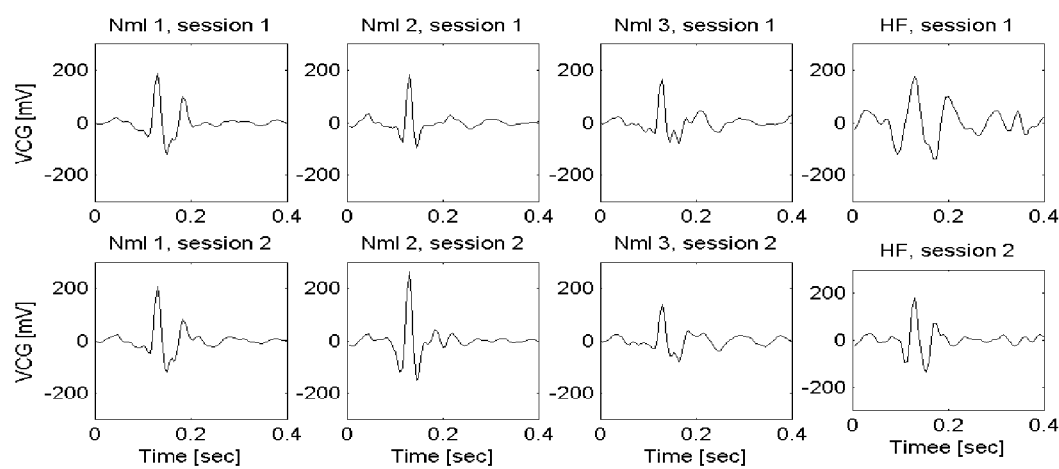
FIG. 9 is a graphical representation showing the mean VCG waveform during two sessions of measurement for four subjects; including three normal subjects (first 3 columns) and one heart failure patient (last column).

FIG. 9 shows the mean VCG waveform during two sessions of measurements for four subjects. The two recording sessions were 24 hours apart for all four subjects. In FIG. 9, the first three subjects (e.g., the first 3 columns of the figure) were normal subjects with a stable cardiac status. The fourth subject (e.g., the last column) had a recovering heart failure. The calculated VCG features (i.e., JI/HI ratio and instantaneous frequency) for all 4 subjects are listed in Table 2 below.

The range of the JI/HI ratio was 2.4 to 3.5 in normal patients and 2.2 to 2.5 in the heart failure (HF) patient. The dominant frequency ranged from 22.7 to 26.6 Hz in normal patients and 15.0 to 25.1 Hz in the HF patient. Overlap in these values is not a major concern when the cardiac monitor 12 is used primarily for detecting changes in clinical status. However, an additional or alternative use for the cardiac monitor 12 is to differentiate between normal patients and HF patients. For example, a recorded VCG waveform for a new patient may be compared with a VCG standard illustrating a patient with and/or without a cardiac condition. In Table 2, the parameter changes in subjects with stable conditions (the normal patients) were smaller than the changes seen when the HF patient status improved. The JI/HI ratio was smaller for the more severe HF state (session 1 compared to session 2 of the HF patient) in this patient. The trend may reverse in other patients. Table 2 shows that the JI/HI ratio changed with clinical status changes more than the changes seen when the clinical status did not change. The data shown in Table 2 illustrates that that the root-mean-square ($RMS_w$) of the difference between waveform pairs (block 210) and instantaneous frequencies around the J waves are sensitive to clinical status changes.

TABLE 2

VCG Amplitude and frequency features during each of the two testing sessions for all 4 subjects

| | Subject | | | | | | | |
|---|---|---|---|---|---|---|---|---|
| | 1 (normal) | | 2 (normal) | | 3 (normal) | | 4 (HF) | |
| Session | 1 | 2 | 1 | 2 | 1 | 2 | 1 | 2 |
| JI/HI | 3.54 | 3.35 | 2.64 | 2.40 | 3.30 | 3.16 | 2.18 | 2.48 |
| Instantaneous frequency [Hz] | 22.7 | 24.0 | 26.6 | 25.2 | 25.1 | 24.1 | 15.0 | 25.1 |

Table 3 shows the calculated inter-session feature changes as well as the $RMS_w$ of the inter-session wave difference. The intra-session parameter changes were also calculated and were smaller than the inter-session values of Table 3. The data of Table 3 shows that VCG varied more significantly when the HF clinical status changed. More specifically, the variation in all three parameters for the HF patient is larger than subjects with stable clinical states (e.g., the first 3 patients). This indicates that all 3 parameters are useful in detecting clinical HF status changes.

TABLE 3

Parameters describing VCG changes between sessions

| Subject | 1 (normal) | 2 (normal) | 3 (normal) | 4 (HF) |
|---|---|---|---|---|
| JI/HI change [%] | 5.7 | 9.3 | 4.1 | 12.9 |
| $RMS_w$ of the waveform difference [% of J wave amplitude] | 4.9 | 6.9 | 9.1 | 34.1 |
| Change in frequency [%] | 5.5 | 5.1 | 4.3 | 50.1 |
| Inter-session variation score | 0.9 | 1.6 | 1.1 | 38.4 |

The changes in the three parameters were on the same order of magnitude because all parameters were normalized (by the waveform amplitude and/or frequency). Parameters were combined into one value and/or variation score (last row in Table 3) using the process 199 shown in FIG. 4. This metric was calculated as one hundred times the sum of the squares of the three original parameters. The data revealed that the variation score was <1.6 when no clinical change was indicated, and was 38.4 when the HF patient clinical status changed. This shows that this metric is useful for detecting HF status changes. Further, combining all three parameters into one variation score simplifies detection of clinical status changes.

Alternatively or additionally, in some examples, a beat-to-beat VCG variation score is calculated and the trend of the variation score and its changes with patient maneuvers or changes in the level of activity is calculated and correlated with the HF state. This is also stored in the memory 40 and used to predict changes in the HF state. These calculations are performed for each patient separately and the patient-specific data is stored to improve predictive accuracy of the device (and limit the noise due to intersubject variability). In this context, adaptive learning algorithms such as a neural network or any other past, present, and/or future methods can be used to train the system using the response of each subject. Data for multiple subjects may be combined in the memory 40 of the cardiac monitor 12 or the remote host to increase universality of the system.

For some heart conditions, patient-to-patient variability may be substantial, which significantly reduces the discriminatory power that a predetermined set of parameter values affords the assessment of the cardiac condition. In some examples, for assessment of cardiac conditions in which variability between patients is relatively high, a set of baseline parameter values may be developed for each patient and relative comparisons of calculated parameter values to these baseline values may be made to more precisely assess the cardiac conditions within that particular patient. For example, to account for intersubject variability, the threshold used in block 216 may be adjusted by the physician and/or patient based on patient history and other available information to maximize accuracy.

Additionally or alternatively, while the sensors in the illustrated example are applied at the skin surface, they can also be implanted. The sensors 31-32 can also be part of a multi-mode apparatus that is non-invasive or that is implantable. For example, the sensors 31-32 can be part of resynchronization or hemodynamic monitoring devices. The latter device, for example, is a pace-maker and/or a monitor that stores and reports patient heart rate, temperature, patient activity, heart chambers systolic and diastolic pressures, thoracic electric impendence, and other parameters. In this case, the cardiac monitor 12 and sensors 31-32 provide more metrics that correlate with the heart status and help in improving patient management.

When aligning individual VCG waveforms (e.g., to calculate the mean VCG, as done by block 308) and an ECG signal is measured, the ECG signal can also serve as a timing signal for alignment. For example, a matched filter or any other alignment approach can be applied to the ECG signal to find the timing of cardiac cycles. These times are then used to align the VCG signal and/or other cardiac signals.

In addition, when ECG is measured, time interval calculations are performed between the different waves in the ECG (including P, Q, R and S) and VCG waves. Similar interval calculations (between acoustic and VCG and/or ECG) can be performed when acoustic signals are measured and S1, S2, S3 and/or S4 timings are determined. When the cardiac monitor 12 is equipped with a chamber pressure measurement component, yet another similar set of interval calculations is performed (e.g., intervals between key blood pressure waves, VCG signals, acoustic and/or ECG waves).

Alternately or additionally, the VCG spatial distribution is also determined using a sensor array or by moving the sensor to other locations. Changes in the distribution are indicative of heart activity changes, which are also reported by the cardiac monitor 12. The distribution can be measured over short (e.g. few centimeters) or longer distances.

An example of the longer distances includes carotid pulse measurements. This measurement allows systolic time interval calculations (including an interval from onset of QRS and aortic second heart sound (Q-S2), left ventricle ejection time (LVET), pre-ejection period (PEP), and ratio of PEP to LVET, which can help in ventricular systolic function assessment.

Acoustic measurements with acoustic sensors such as an electronic stethoscope can also be added. Heart sound acoustic cardiography depends primarily on the detection of S3, which has only modest sensitivity to HF. S3 can be heard in patients with and without HF, but S3 usually occurs more in HF patients. Another limitation of using S3 (and/or S4) alone for detecting HF class change is the prevalence of S3 alteration resulting from HF patient therapy. The effectiveness of S3 for HF monitoring is likely limited due to the large percentage of HF patients without manifestation of a third or fourth heart sound. Time intervals between VCG, ECG, and/or heart sounds measured at different locations can be calculated. For example, measurements can be performed at the chest surface and over the radial or femoral arteries and inter-sensor time intervals between different waves (PQRS, GHKJKLMN, S1, S2, S3, S4, pressure waves, etc) are calculated.

While the cardiac monitor 12 shown in FIGS. 1 and 2 is described by way of example as being adapted to process the vibro-acoustic signals acquired by the sensors 31-32 using digital signal processing techniques, which often provides more flexibility, analog signal processing techniques may be used instead to process vibration or sound information to achieve the same or similar results. For example, an analog filter(s) may be used to separate the energy associated with different energy bands, amplifiers may be used to change waveform amplitudes, and circuits may also be used to subtract waveforms, determine RMS values, and find ratios between amplitudes. In addition, dominant frequencies may be calculated from the time intervals between zero crossings.

The computational code that performs required calculations can be implemented in any machine programming language such as Assembly, C/C++, Basic, Fortran, Matlab, Labview, etc. In some implementations, Assembly machine language is used as it allows for precise timing and reduction of system delays.

Additionally or alternatively, other VCG metrics can be derived from time-frequency analysis such as wavelet analysis or time-dependent spectrogram that may be calculated using short-term fast-Fourier transform. For example, time-frequency surfaces (representing the signal amplitude at each time and frequency) can be aligned temporally using, for example, matched filters and a surface representing the mean amplitude as a function of time and frequency is determined. The dominant frequency at any time such as the J peak can be determined. The time evolution (beat-to-beat and trends over minutes, hours, and days) of the different metrics (such as the dominant frequency and amplitude of the J, JI/HI, etc.) can be also extracted from the time-frequency decompositions.

While in the described examples sensors are primarily placed on the chest to monitor heart and heart muscle activity, the sensors can also be placed at any other location such as, for example, on a muscle. In this case, the utility of the apparatus and methods described herein also extend to diagnosing and screening for neuromuscular diseases such as seizure disorders, degenerative diseases, Guillian-Barre, Myasthenia Gravis, multiple sclerosis, and amyotrophic lateral sclerosis. Other examples of utility include rehabilitation medicine, evaluation and biofeedback, evaluation of muscle sports or trauma injury, muscular dystrophy, inflammation of muscles, pinched nerves, peripheral nerve damage (damage to nerves in the arms and legs), disc herniation, amyotrophic lateral sclerosis, anterior compartment syndrome, axillary nerve dysfunction, Becker's muscular dystrophy, brachial plexopathy, carpal tunnel syndrome, centronuclear myopathy, cervical spondylosis, Charcot-Marie-Tooth disease, chronic Immune demyelinating coly [radiculo] neuropathy (CIDP), common peroneal nerve dysfunction, denervation (reduced nervous stimulation), dermatomyositis, distal median nerve dysfunction, duchenne muscular dystrophy, facioscapulohumeral muscular dystrophy (Landouzy-Dejerine), familial periodic paralysis, femoral nerve dysfunction, fields condition, Friedreich's ataxia, Guillain-Barre Lambert-Eaton syndrome, Mononeuritis multiplex, mononeuropathy, motor neurone disease, multiple system atrophy, myasthenia gravis, myopathy (muscle degeneration, which may be caused by a number of disorders, including muscular dystrophy), myotubular myopathy, neuromyotonia, peripheral neuropathy, poliomyelitis, polymyositis, radial nerve dysfunction, sciatic nerve dysfunction, sensorimotor polyneuropathy, sleep bruxism, spinal stenosis, thyrotoxic periodic paralysis, tibial nerve dysfunction, and ulnar nerve dysfunction.

The cardiac monitor 12 is also useful for diagnosis and screening of orthopedic and joint conditions such as: traumatic injury evaluation and rehab, arthritis including: osteoarthritis (also known as degenerative joint disease), other arthritides: septic (infections), rheumatoid, psoriatic, autoimmune, inflammatory bowel disease, gout and pseudogout (formation of rhomboidal shaped crystals of calcium pyrophosphate).

Figure 10:
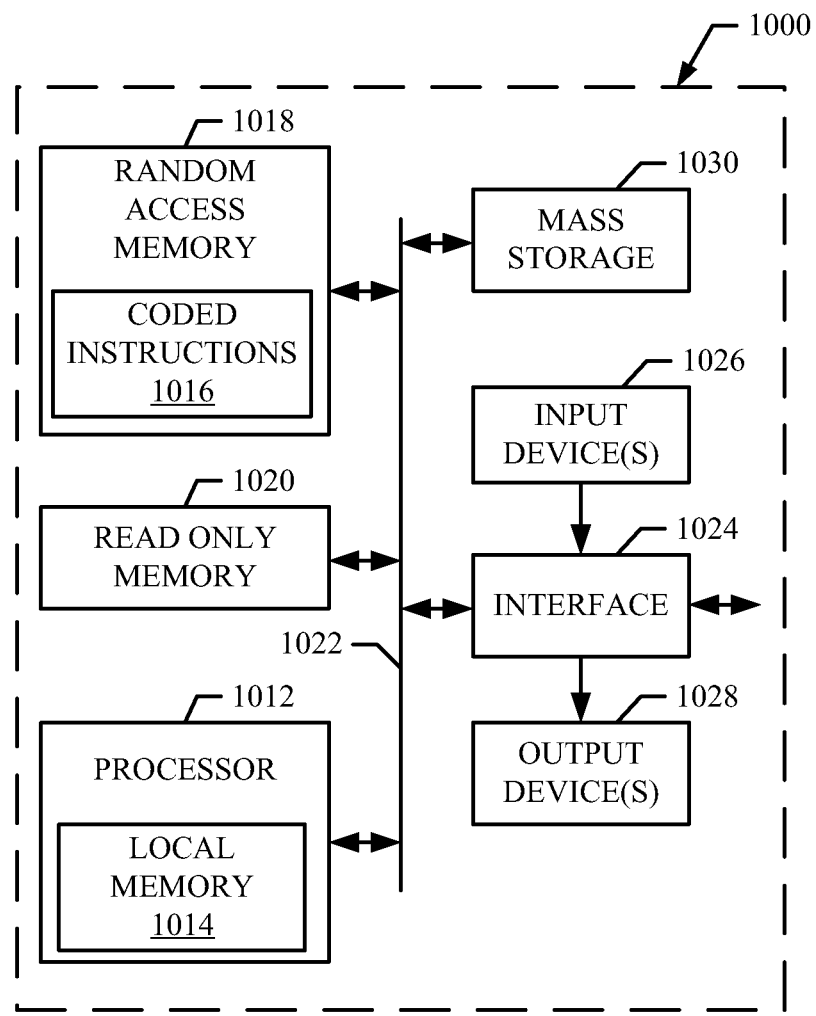
FIG. 10 is a block diagram of an example processor system that may be used to implement the example apparatus and methods described herein.

FIG. 10 is a block diagram of an example processor platform 1000 capable of implementing the apparatus and methods disclosed herein. The processor platform 1000 can be, for example, a server, a personal computer, a personal digital assistant (PDA), a cell phone, an Internet appliance, a dedicated device, or any other type of computing device.

The system 1000 of the instant example includes a processor 1012 such as a general purpose programmable processor. The processor 1012 includes a local memory 1014, and executes coded instructions 1016 present in the local memory 1014 and/or in another memory device. The processor 1012 may execute, among other things, the processes instructions represented in FIGS. 3-6. The processor 1012 may be any type of processing unit, such as one or more microprocessors from the Intel® Centrino® family of microprocessors, the Intel® Pentium® family of microprocessors, the Intel® Itanium® family of microprocessors, and/or the Intel XScale® family of processors. Of course, other processors from other families are also appropriate.

The processor 1012 is in communication with a main memory including a volatile memory 1018 and a non-volatile memory 1020 via a bus 1022. The volatile memory 1018 may be implemented by Static Random Access Memory (SRAM), Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1020 may be implemented by flash memory and/or any other desired type of memory device. Access to the main memory 1018, 1020 is typically controlled by a memory controller (not shown).

The processor platform 1000 also includes an interface circuit 1024. The interface circuit 1024 may be implemented by any type of interface standard, such as an Ethernet interface, a universal serial bus (USB), and/or a third generation input/output (3GIO) interface.

One or more input devices 1026 are connected to the interface circuit 1024. The input device(s) 1026 permit a user to enter data and commands into the processor 1012. The input device(s) can be implemented by, for example, a keyboard, a mouse, a touchscreen, a track-pad, a trackball, an isopoint, and/or a voice recognition system.

One or more output devices 1028 are also connected to the interface circuit 1024. The output devices 1028 can be implemented, for example, by display devices (e.g., a liquid crystal display, a cathode ray tube display (CRT)), by a printer and/or by speakers. The interface circuit 1024, thus, typically includes a graphics driver card.

The interface circuit 1024 also includes a communication device such as a modem or network interface card to facilitate exchange of data with external computers via a network (e.g., an Ethernet connection, a digital subscriber line (DSL), a telephone line, coaxial cable, a cellular telephone system, etc.).

The processor platform 1000 also includes one or more mass storage devices 1030 for storing software and data. Examples of such mass storage devices 1030 include floppy disk drives, hard drive disks, compact disk drives and digital versatile disk (DVD) drives. The mass storage device 1030 may implement the example memory 40. Alternatively, the volatile memory 1018 may implement the example memory 40.

As an alternative to implementing the methods and/or apparatus described herein in a system such as the device of FIG. 10, the methods and or apparatus described herein may be embedded in a structure such as a processor and/or an ASIC (application specific integrated circuit). As discussed above, some implementations utilize a small form factor processor for the cardiac monitor 12, however any structure could additionally or alternatively be used.

Although the above discloses example systems including, among other components, software executed on hardware, it should be noted that such systems are merely illustrative and should not be considered as limiting. For example, it is contemplated that any or all of the disclosed hardware and software components could be embodied exclusively in dedicated hardware, exclusively in software, exclusively in firmware or in some combination of hardware, firmware and/or software.

We claim:

1. A method to detect a cardiac condition, the method comprising:
   calculating, with a processor, a frequency difference between a first frequency of a first cardiac signal and a second frequency of a second cardiac signal, wherein the first and second cardiac signals are vibrocardiography signals;
   calculating, with the processor, an amplitude difference between the first cardiac signal and the second cardiac signal, wherein calculating the amplitude difference comprises calculating a difference between a first amplitude ratio and a second amplitude ratio;
   calculating, with the processor, a root-mean-square value based on a difference between the first cardiac signal and the second cardiac signal;
   calculating, with the processor, a value based on the frequency difference, the amplitude difference, and the root-mean-square value; and detecting a cardiac condition based on the value.

2. The method as described in claim 1, further comprising calculating the first amplitude ratio and the second amplitude ratio using respective J, H and I peaks of the respective first and second cardiac signals.

3. The method as described in claim 2, wherein calculating the first amplitude ratio comprises:
    calculating a first difference between an amplitude of a J peak of the first cardiac signal and an amplitude of an I peak of the first cardiac signal;
    calculating a second difference between the amplitude of the I peak of the first cardiac signal and an amplitude of an H peak of the first cardiac signal; and
    dividing the first difference by the second difference.

4. The method as described in claim 2, wherein calculating the second amplitude ratio comprises:
    calculating a third difference between an amplitude of a J peak of the second cardiac signal and an amplitude of an I peak of the second cardiac signal;
    calculating a fourth difference between an amplitude of the I peak of the second cardiac signal and an amplitude of an H peak of the second cardiac signal; and
    dividing the third difference by the fourth difference.

5. The method as described in claim 1, further comprising normalizing the amplitude difference.

6. The method as described in claim 1, further comprising:
    normalizing the first cardiac signal by an amplitude of a J peak of the first cardiac signal to form a first normalized cardiac signal;
    normalizing the second cardiac signal by an amplitude of a J peak of the second cardiac signal to form a second normalized cardiac signal; and
    calculating the root-mean-square value based on the difference between the first cardiac signal and the second cardiac signal by calculating a difference between the first normalized cardiac signal and the second normalized cardiac signal.

7. The method as described in claim 1, further comprising temporally aligning the first cardiac signal and the second cardiac signal prior to calculating the root-mean-square value.

8. The method as described in claim 7, wherein temporally aligning the first cardiac signal and the second cardiac signal comprises using a J peak of the first cardiac signal and a J peak of the second cardiac signal.

9. The method as described in claim 1, wherein the first frequency of the first cardiac signal is an instantaneous frequency adjacent a J peak of the first cardiac signal.

10. The method as described in claim 9, further comprising calculating the instantaneous frequency using a Hilbert transform.

11. The method as described in claim 1, wherein detecting the cardiac condition based on the value comprises comparing the value to a threshold associated with a heart condition.

12. The method as described in claim 1, wherein the first cardiac signal is indicative of a first breathing phase and the second cardiac signal is indicative of a second breathing phase.

13. The method as described in claim 12, wherein the first breathing phase is an inspiratory phase and the second breathing phase is an expiratory phase.

14. The method as described in claim 12, wherein the first breathing phase is an inspiratory phase and the second breathing phase is an inspiratory phase.

15. The method as described in claim 1, wherein the first cardiac signal is a mean of a received cardiac signal.

16. The method as described in claim 15, wherein determining the mean of the received cardiac signal comprises sampling a plurality of cardiac cycles.

17. The method as described in claim 1, wherein:
    the second cardiac signal is indicative of a sequential cardiac cycle after the first cardiac signal; and
    the value represents a beat-to-beat variability.

18. The method as described in claim 1, wherein the cardiac signals are acquired from a patient involved in an activity.

19. The method as described in claim 18, wherein the activity is standing.

20. The method as described in claim 18, wherein the activity is a valsalva maneuver.

21. The method as described in claim 1, wherein calculating the at least one of the frequency difference and the amplitude difference comprises performing a time-frequency analysis.

22. The method as described in claim 1, wherein the first cardiac signal is measured at a first location of a patient and the second cardiac signal is measured at a second location of the patient different than the first location.

23. The method as described in claim 1, wherein the first cardiac signal is received at a first time and the second cardiac signal is received at a second time different from the first time.

24. The method as described in claim 23, wherein a difference between the first time and the second time is greater than one hour.

25. A method to detect a cardiac condition, the method comprising:
    calculating, with a processor, a frequency difference between a first frequency of a first cardiac signal and a second frequency of a second cardiac signal, wherein the first and second cardiac signals are vibrocardiography signals;
    calculating, with the processor, an amplitude difference between the first cardiac signal and the second cardiac signal;
    calculating, with the processor, a root-mean-square value based on a difference between the first cardiac signal and the second cardiac signal;
    calculating, with the processor, a value based on the frequency difference, the amplitude difference, and the root-mean-square value, wherein calculating the value comprises calculating a sum of squares of the frequency difference, the amplitude difference, and the root-mean-square value; and
    detecting a cardiac condition based on the value.

26. The method as described in claim 25, wherein the sum is a weighted sum.

27. A method to detect a cardiac condition, the method comprising:
    receiving an electrocardiographic signal;
    calculating a time difference between a peak of a first cardiac signal and a peak of the electrocardiographic signal;
    calculating, with a processor, a frequency difference between a first frequency of the first cardiac signal and a second frequency of a second cardiac signal, wherein the first and second cardiac signals are vibrocardiography signals;
    calculating, with the processor, an amplitude difference between the first cardiac signal and the second cardiac signal;
    calculating, with the processor, a root-mean-square value based on a difference between the first cardiac signal and the second cardiac signal;

calculating, with the processor, a value based on the frequency difference, the amplitude difference, and the root-mean-square value; and
detecting a cardiac condition based on the value.

28. A method to detect a cardiac condition, the method comprising:
receiving an acoustic signal;
calculating a time difference between a peak of a first cardiac signal and a peak of the acoustic signal;
calculating, with a processor, a frequency difference between a first frequency of the first cardiac signal and a second frequency of a second cardiac signal, wherein the first and second cardiac signals are vibrocardiography signals;
calculating, with the processor, an amplitude difference between the first cardiac signal and the second cardiac signal;
calculating, with the processor, a root-mean-square value based on a difference between the first cardiac signal and the second cardiac signal;
calculating, with the processor, a value based on the frequency difference, the amplitude difference, and the root-mean-square value; and
detecting a cardiac condition based on the value.

29. A method to detect a cardiac condition, the method comprising:
calculating, with a processor, a frequency difference between a first frequency of a first cardiac signal and a second frequency of a second cardiac signal, wherein the first cardiac signal and the second cardiac signal are vibrocardiography signals;
calculating, with the processor, an amplitude difference between the first cardiac signal and the second cardiac signal;
calculating, with the processor, a root-mean-square value based on a difference between the first cardiac signal and the second cardiac signal;
calculating, with the processor, a value based on the frequency difference, the amplitude difference, and the root-mean-square value;
detecting a cardiac condition based on the value; and
calculating a score based on the value and at least one previously calculated value, wherein the score represents a degree of clinical intervention.

30. A method to detect a cardiac condition, the method comprising:
calculating, with a processor, a frequency difference between a first frequency of a first cardiac signal and a second frequency of a second cardiac signal, wherein the first cardiac signal and the second cardiac signal are vibrocardiography signals;
calculating, with the processor, an amplitude difference between the first cardiac signal and the second cardiac signal;
calculating, with the processor, a root-mean-square value based on a difference between the first cardiac signal and the second cardiac signal;
calculating, with the processor, a value based on the frequency difference, the amplitude difference, and the root-mean-square value;
detecting a cardiac condition based on the value;
obtaining a first cardiac signal template from a memory;
filtering the first cardiac signal based on the first cardiac signal template;
identifying a first cardiac event within the filtered first cardiac signal;
identifying a second cardiac event within the filtered first cardiac signal;
determining a first mean of the cardiac events;
temporally aligning the cardiac events based on the first mean and the first cardiac signal template; and
determining a second mean of the temporally aligned cardiac events, the second mean being at least part of a second cardiac signal template.

31. The method as described in claim 30, wherein the first cardiac signal is received via an accelerometer coupled to a patient.

32. The method as described in claim 30, wherein a subsequent detection of a cardiac event uses the second cardiac signal template.

33. The method as described in claim 30, wherein identifying the first cardiac event comprises receiving an input from a user indicative of the first cardiac event.

34. A method to detect a cardiac condition, the method comprising:
calculating, with a processor, a frequency difference between a first frequency of a first cardiac signal and a second frequency of a second cardiac signal, wherein the first cardiac signal is indicative of a first breathing phase and the second cardiac signal is indicative of a second breathing phase, wherein the first breathing phase is an expiratory phase and the second breathing phase is an expiratory phase, wherein the first cardiac signal and the second cardiac signal are vibrocardiography signals;
calculating, with the processor, an amplitude difference between the first cardiac signal and the second cardiac signal;
calculating, with the processor, a root-mean-square value based on a difference between the first cardiac signal and the second cardiac signal;
calculating, with the processor, a value based on the frequency difference, the amplitude difference, and the root-mean-square value; and
detecting a cardiac condition based on the value.

35. A method to detect a cardiac condition, the method comprising:
calculating, with a processor, a frequency difference between a first frequency of a first cardiac signal and a second frequency of a second cardiac signal, wherein the first cardiac signal and the second cardiac signal are vibrocardiography signals;
filtering the first cardiac signal using a band pass filter;
calculating, with the processor, an amplitude difference between the first cardiac signal and the second cardiac signal, wherein calculating the amplitude difference comprises calculating a difference between a first amplitude ratio and a second amplitude ratio;
calculating, with the processor, a root-mean-square value based on a difference between the first cardiac signal and the second cardiac signal;
calculating, with the processor, a value based on the frequency difference, the amplitude difference, and the root-mean-square value; and
detecting a cardiac condition based on the value.

36. A tangible machine-readable storage medium comprising instructions which, when executed, cause a machine to at least:
calculate a frequency difference between a first frequency of a first cardiac signal and a second frequency of a second cardiac signal, wherein the first cardiac signal and the second cardiac signal are vibrocardiography signals;

calculate an amplitude difference between the first cardiac signal and the second cardiac signal, wherein calculating the amplitude difference comprises calculating a difference between a first amplitude ratio and a second amplitude ratio;

calculate a root-mean-square value based on a difference between the first cardiac signal and the second cardiac signal;

calculate a value based on the frequency difference, the amplitude difference, and the root-mean-square value; and detect a cardiac condition based on the value.

37. The machine-readable storage medium as described in claim 36, further comprising instructions which when executed cause the machine to calculate the first amplitude ratio and the second amplitude ratio using respective J, H and I peaks of the respective first and second cardiac signals.

38. The machine-readable storage medium as described in claim 37, further comprising instructions which, when executed, cause the machine to at least:

calculate a first difference between an amplitude of a J peak of the first cardiac signal and an amplitude of an I peak of the first cardiac signal;

calculate a second difference between the amplitude of the I peak of the first cardiac signal and an amplitude of an H peak of the first cardiac signal; and divide the first difference by the second difference.

39. The machine-readable storage medium as described in claim 37, further comprising instructions which, when executed, cause the machine to at least:

calculate a third difference between an amplitude of a J peak of the second cardiac signal and an amplitude of an I peak of the second cardiac signal;

calculate a fourth difference between an amplitude of the I peak of the second cardiac signal and an amplitude of an H peak of the second cardiac signal; and divide the third difference by the fourth difference.

40. The machine-readable storage medium as described in claim 36, further comprising instructions which, when executed, cause the machine to at least:

normalize the first cardiac signal by an amplitude of a J peak of the first cardiac signal to form a first normalized cardiac signal;

normalize the second cardiac signal by an amplitude of a J peak of the second cardiac signal to form a second normalized cardiac signal; and calculate the root-mean-square value based on the difference between the first cardiac signal and the second cardiac signal by calculating a difference between the first normalized cardiac signal and the second normalized cardiac signal.

41. The machine-readable storage medium as described in claim 36, further comprising instructions which, when executed, cause the machine to temporally align the first cardiac signal and the second cardiac signal prior to calculating the root-mean-square value.

42. The machine-readable storage medium as described in claim 41, wherein temporally aligning the first cardiac signal and the second cardiac signal comprises using a J peak of the first cardiac signal and a J peak of the second cardiac signal.

43. The machine-readable storage medium as described in claim 36, further comprising instructions which, when executed, cause the machine to compare the value to a threshold associated with a heart condition.

44. The machine-readable storage medium as described in claim 36, wherein the first cardiac signal is indicative of a first breathing phase and the second cardiac signal is indicative of a second breathing phase.

45. The machine-readable storage medium as described in claim 36, further comprising instructions which, when executed, cause the machine to at least:

receive an electrocardiographic signal; and calculate a time difference between a peak of the first cardiac signal and a peak of the electrocardiographic signal.

46. The machine-readable storage medium as described in claim 36, further comprising instructions which, when executed, cause the machine to at least:

receive an acoustic signal; and calculate a time difference between a peak of the first cardiac signal and a peak of the acoustic signal.

47. A tangible machine-readable storage medium comprising instructions which, when executed, cause a machine to at least:

calculate a frequency difference between a first frequency of a first cardiac signal and a second frequency of a second cardiac signal, wherein the first cardiac signal and the second cardiac signal are vibrocardiography signals;

calculate an amplitude difference between the first cardiac signal and the second cardiac signal;

calculate a root-mean-square value based on a difference between the first cardiac signal and the second cardiac signal;

calculate a value based on the frequency difference, the amplitude difference, and the root-mean-square value;

detect a cardiac condition based on the value; and calculate a score based on the value and at least one previously calculated value, wherein the score represents a degree of clinical intervention.

48. A tangible machine-readable storage medium comprising instructions which, when executed, cause a machine to at least:

receive an electrocardiographic signal;

calculate a time difference between a peak of a first cardiac signal and a peak of the electrocardiographic signal;

calculate a frequency difference between a first frequency of the first cardiac signal and a second frequency of a second cardiac signal, wherein the first and second cardiac signals are vibrocardiography signals;

calculate an amplitude difference between the first cardiac signal and the second cardiac signal;

calculate a root-mean-square value based on a difference between the first cardiac signal and the second cardiac signal;

calculate a value based on the frequency difference, the amplitude difference, and the root-mean-square value; and detect a cardiac condition based on the value.

49. A tangible machine-readable storage medium comprising instructions which, when executed, cause a machine to at least:

receive an acoustic signal;

calculate a time difference between a peak of a first cardiac signal and a peak of the acoustic signal;

calculate a frequency difference between a first frequency of the first cardiac signal and a second frequency of a second cardiac signal, wherein the first and second cardiac signals are vibrocardiography signals;

calculate an amplitude difference between the first cardiac signal and the second cardiac signal;

calculate a root-mean-square value based on a difference between the first cardiac signal and the second cardiac signal;

calculate a value based on the frequency difference, the amplitude difference, and the root-mean-square value; and detect a cardiac condition based on the value.

\* \* \* \* \*